(12) United States Patent
Prime et al.

(10) Patent No.: US 6,644,313 B2
(45) Date of Patent: Nov. 11, 2003

(54) BREATHING ASSISTANCE APPARATUS

(75) Inventors: Neil Prime, Auckland (NZ); Martin Leckie, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 10/056,827

(22) Filed: Jan. 25, 2002

(65) Prior Publication Data

US 2002/0100478 A1 Aug. 1, 2002

(30) Foreign Application Priority Data

Feb. 1, 2001 (NZ) .................................................. 509706

(51) Int. Cl.$^7$ .............................................. A62B 9/02
(52) U.S. Cl. ........................... 128/205.24; 128/204.17; 128/204.18; 137/383
(58) Field of Search ....................... 128/205.24, 203.14, 128/204.17, 204.26, 201.28, 204.18; 137/908, 505.11, 505.14, 383, 384, 384.2, 384.4, 384.6, 384.8, 385; 251/89, 104, 105

(56) References Cited

U.S. PATENT DOCUMENTS

| | | | | |
|---|---|---|---|---|
| 685,396 A | * | 10/1901 | Dexter ........................ | 137/382 |
| 1,099,280 A | * | 6/1914 | Connolly ..................... | 70/177 |
| 1,482,517 A | * | 2/1924 | Kelsey ........................ | 137/224 |
| 1,743,350 A | * | 1/1930 | Hopkins ...................... | 137/382 |
| 1,795,839 A | * | 3/1931 | Credle ......................... | 70/175 |
| 2,364,812 A | * | 12/1944 | Pierson ........................ | 137/469 |
| 2,755,817 A | * | 7/1956 | Barr ............................ | 137/536 |
| 3,253,612 A | * | 5/1966 | Curatola et al. ............ | 137/553 |
| 3,272,218 A | * | 9/1966 | Johnson ...................... | 137/102 |
| 3,593,549 A | * | 7/1971 | Lakins et al. ................ | 70/164 |
| 3,601,362 A | * | 8/1971 | Gunther ...................... | 251/285 |
| 3,796,228 A | * | 3/1974 | Bedo et al. .................. | 137/536 |
| 3,882,884 A | * | 5/1975 | Leopold et al. ............. | 137/327 |
| 3,903,881 A | * | 9/1975 | Weigl ..................... | 128/204.25 |
| 4,004,603 A | * | 1/1977 | Jones ........................... | 137/107 |
| 4,026,284 A | * | 5/1977 | Boehringer ............. | 128/205.24 |
| 4,044,793 A | * | 8/1977 | Krueger et al. ............. | 137/881 |
| 4,483,366 A | * | 11/1984 | Labita ........................ | 137/385 |
| 4,515,179 A | * | 5/1985 | Edmunds et al. ...... | 137/543.13 |
| 4,823,828 A | * | 4/1989 | McGinnis .................... | 137/102 |
| 5,190,070 A | * | 3/1993 | Robinson .................... | 137/385 |
| 5,275,153 A | * | 1/1994 | Kay ........................ | 128/205.24 |
| 5,313,975 A | * | 5/1994 | Nimberger .................. | 137/14 |
| 5,568,910 A | * | 10/1996 | Koehler et al. ................ | 251/83 |
| 5,664,447 A | | 9/1997 | Neeley ......................... | 70/175 |
| 5,743,257 A | * | 4/1998 | Koehler et al. ......... | 128/205.24 |
| 5,931,159 A | * | 8/1999 | Suzuki et al. .......... | 128/204.18 |
| 5,950,623 A | * | 9/1999 | Michell ................. | 128/205.24 |
| 6,024,120 A | * | 2/2000 | Yam et al. ................... | 137/495 |
| 6,116,278 A | * | 9/2000 | Baumgardner et al. | 137/625.25 |

FOREIGN PATENT DOCUMENTS

| | | | | |
|---|---|---|---|---|
| GB | 2121470 A | * | 12/1983 | ........... F16K/35/06 |
| GB | 2121929 A | * | 1/1984 | ........... F16K/35/00 |
| GB | 2230075 A | * | 10/1990 | ........... F16K/35/10 |

* cited by examiner

*Primary Examiner*—Weilun Lo
*Assistant Examiner*—Mital Patel
(74) *Attorney, Agent, or Firm*—Trexler, Bushnell, Giangiorgi, Blackstone & Marr, Ltd.

(57) ABSTRACT

A pressure regulating device for use with a breathing assistance apparatus which conveys gases to a patient requiring breathing assistance. The device includes a valve member disposed within a valve housing which when gases flowing through the regulator reach a predetermined level at least a portion of the gases are permitted to flow through a vent aperture externally, similar to known pressure relief valves. The present invention includes an adjustment mechanism engaged with the valve member and for adjusting the predetermined level, and a locking mechanism for permanently preventing access to the adjustment mechanism once the predetermined level has been factory set.

10 Claims, 3 Drawing Sheets

BREATHING ASSISTANCE APPARATUS

FIELD OF THE INVENTION

The present invention relates to the use of a pressure regulator in conjunction with a breathing assistance apparatus, particularly though not solely, for regulating the pressure of gases supplied to a patient from a humidified Positive End Expiratory Pressure (PEEP) apparatus.

BACKGROUND ART

At the moment of their first breath, a baby's lungs are collapsed and filled with fluid. The pressures needed to open such lungs, and keep them open, are several times that of a normal breath until the fluid is displaced and the lungs have filled with air. To generate these large pressures, the baby must have strong respiratory muscles, as well as a chemical called surfactant in their alveoli. Surfactant reduces the surface tension of the fluid within the alveoli, preventing the alveolar walls from sticking to each other, like coasters to coffee cups when there is water between them.

Neonates have difficulty in opening their lungs and keeping them open. Reasons for this include:

a) Weak respiratory muscles and low surfactant levels. This means that they cannot generate enough pressure to open the lungs and, should they be resuscitated, tire quickly with the effort of keeping open alveoli lacking in surfactant.

b) Underdeveloped internal tissue structure to support the alveoli.

c) Slower clearance of lung fluid. In very premature neonates, fluid may continue to be secreted in the alveoli even after birth.

d) A soft chest wall, horizontal ribs, and a flatter diaphragm contribute to reduce the inspiratory capacity.

e) The mixing of oxygenated and deoxygenated blood raises blood pressure in the lungs, increasing fluid movement from the blood vessels into the lung tissue. The reduced blood oxygen level starves tissue of oxygen and further weakens respiratory muscles.

f) Weak neck muscles and a lack of neck fat reduce upper airway stability so that collapse on inspiration may occur.

g) Collapsed, damaged alveoli secrete proteins that reduce surfactant function.

To alleviate this it is know to apply positive end expiratory pressure (PEEP) during respiration. In applying PEEP, the neonate's upper airway and lungs are held open during inspiration, while expiration occurs against a pressure that stops alveolar collapse. Lung fluid is pushed back into the circulating blood, alveolar surfactant is conserved, and a larger area of the lung participates in gas exchange with the blood. As blood oxygenation and carbon dioxide removal improves, more oxygen is delivered to growing tissues, while less oxygen and energy is consumed by respiratory muscles.

PEEP therapy is known to cause lung rupture (or pneumothorax) in 0–30% of nasally ventilated neonates with air embolism in the vasculature also known to occur. It was originally thought that air would leak out of the mouth should pressures become to high, and therefore the cause of the ruptures was unclear. Perhaps chin-straps, which are used to stop mouth leak and pressure loss, were used on those neonates who later developed pneumothoraaes. Alternatively, it may be that mouth leak never occurs, even under high pressures, because the neonates are obligatory nose-breathers.

To avoid such side effects it is thought desirable in the art to provide a pressure relief valve as a safety device to prevent the pressure rising above a maximum safe level. Accordingly it is well known in the art to use a spring biased valve which actuates at a level of pressure deemed the maximum permissible to allow the gases to vent eternally. This in turn requires the use of high quality springs which have been individually tested to give a high tolerance spring constant in order to ensure that it actuates at a value substantially that of the maximum safe pressure. Both the manufacture and testing of such a spring necessitates that its cost will be correspondingly high. Accordingly it would be advantageous to provide a pressure relief valve for a breathing assistance system which did not involve the use of such a high tolerance spring.

For example in U.S. Pat. No. 4,515,179 a pressure relief valve including a housing defining an internal valve chamber is described. A valve seat is positioned within the chamber, and a valve pallet is reciprocally mounted within the chamber to engage the seat in a valve closed mode. A spring is mounted with in the housing to bias the valve pallet into engagement with the valve seat. A spring retainer is threaded through an aperture in the housing and extends into the valve chamber. The spring is located with in the retainer. A desired set pressure to be imposed upon the valve pallet is provided by threading the retainer relative to the housing thereby compressing the springs. To lock the retainer relative to the housing an annular lock member is threaded onto the outside of the retainer. Once the desired set pressure is attained, the lock member is threaded on the retainer until it abuts the housing. The lock member includes first and second ends spaced apart to define a gap. A fastener is threaded into the first and second ends across the gap and maybe tightened to narrow the gap and set the lock member onto the retainer. The retain is then locked relative to the housing by a jamming screw threaded through the lock member into engagement with housing. To provide better control of the spring an alternative retainer may be employed. The alternative retained includes a pair of telescoping tubes with the spring positioned with in the tubes. A first tube of the pair extends through end is threaded in a bushing mounted in an aperture in the valve housing. A second tube is connected by a gimbal mounting to the valve pallet. An alternative lock member may be secured to the retain by a radial fastener.

In U.S. Pat. No. 5,664,447 a lockout device is disclosed to prevent tampering with the manually set position of a valve or regulating or other device having a rotatable shaft for adjusting, for example, the flow of fluid through the device, from a position initially set to some other position. The lockout device is usable with a wide range of standard valves and regulators which have a drive stem and includes a drive gear that engages the drive sten and a key locking device mounted in a generally cylindrical handle of the lockout device and being selectively movable from first position in which the handle free-wheels relative to the drive stem of the valve so as to prevent unauthorized moving of the rotational position of the valve stem by any person not having a key to an engaging position in which the handle is locked to the drive stem to permit ordinary rotational movement and setting of the valve stem position.

In U.S. Pat. No. 5,950,623 an adjustable pressure limiting valve having a non-linear biasing means is described. The valve has a movable valve member that can be moved to an open position by a predetermined pressure and a closed position on a valve seat. A rotating control knob is rotated by the use to adjust the bias acting against the movable valve member toward the closed position to, in turn, set the pressure at which the valve opens. A rotating cylindrical drum rotates along with the control knob and has a helical groove formed in its exterior and a pair of fixed pins that ride in the helical groove. When the cylindrical drum is rotated, the fixed pins riding in the helical grove cause the cylindrical drum to move along its longitudinal axis to compress or decompress a spring acting against the movable valve member. The relationship between the rotational movement of the control knob and the longitudinal movement of the cylindrical drum.

SUMMARY OF THE INVENTION

It is an object of the present invention to provide a pressure regulator which goes some way to overcoming the above-mentioned disadvantages, or which will at least provide the Healthcare industry with a useful choice.

Accordingly, in a first aspect, the present invention consists in a pressure regulating device for use with a breathing assistance apparatus which conveys gases to a patient requiring breathing assistance, comprising or including:

housing means including an inlet and an outlet and a venting aperture, in use said inlet and outlet being in fluid communication or integrated with one of said conduits, a valve member disposed within said housing means, in the flow path between said inlet and said outlet, wherein the pressure of gases flowing from said inlet to said outlet being below a predetermined level said valve member blocking said vent aperture and said gases thereby flowing from said inlet to said outlet, and wherein said gases being above said predetermined level said valve member allowing at least a portion of said gases to flow through said vent aperture, adjustment means engaged with said valve member and adapted to adjust said predetermined level, and adjustment locking means which once installed on or about said adjustment means, permanently locking said adjustment means in place, such that said predetermined level is permanently set.

Preferably said valve means comprises a valve housing, a valve member and a restraining means wherein said pressure of gases flowing from said inlet to said outlet being below said predetermined level said restraining means biasing said valve member against said vent aperture thereby blocking said vent aperture, and wherein the pressure of said gases being above said predetermined level said restraining means biasing said valve member to a position to allow at least a portion of said gases through said vent aperture.

Preferably said adjustment means comprises a rotatable cap engaged with said valve member, said restraining means and said valve housing, whereby the rotation of said cap with respect to said valve housing changes the compression of said restraining means thereby changing said predetermined level.

Preferably said locking means comprises a further cap which is adapted to fit over the top of said adjusting cap wherein with said further cap installed over top of said adjusting cap, said adjusting cap is prevented from external access and prevented from further rotation.

In a second aspect, the present invention consists in a breathing assistance apparatus for supplying gases to a patient to assist said patient's breathing including: gases supply means adapted to supply gases to said patient, delivery means including a plurality of ports adapted to deliver said flow of gases to said patient, inhalatory gases transport means for conveying said flow of gases from said gases supply means to said delivery means, and a pressure regulating device disposed within or in fluid communication with said inhalatory gases transport means, said pressure regulating device comprising or including:

housing means including an inlet and an outlet and a venting aperture, in use said inlet and outlet being in fluid communication or integrated with said inhalatory gases transport means, a valve member disposed within said housing means, in the flow path between said inlet and said outlet, wherein the pressure of gases flowing from said inlet to said outlet being below a predetermined level said valve member blocking said vent aperture and said gases thereby flowing from said inlet to said outlet, and wherein said gases being above said predetermined level said valve member allowing at least a portion of said gases to flow through said vent aperture, adjustment means engaged with said valve member and adapted to adjust said predetermined level, and adjustment locking means which once installed on or about said adjustment means, permanently locking said adjustment means in place, such that said predetermined level is permanently set.

Preferably said apparatus further comprises humidification means disposed within or in fluid communication with said gases supply means, said inhalatory gases transport means and said delivery means, thereby humidifying said gases.

In a third aspect the present invention consists of a method of manufacturing a system for regulating the pressure of gases supplied to a patient to assist said patents breathing comprising the steps:

providing a valve to relieve the pressure of said gases substantially at a predetermined pressure adjusting said predetermined pressure to a desired pressure, and preventing further access to the adjustment such that said predetermined pressure is permanently set.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

The present invention provides a means of regulating the pressure of gases supplied to a patient connected to a positive pressure ventilation device to a maximum safe level. By providing an adjustable pressure relief valve the need for an expensive spring is avoided. The adjustment is made during manufacture and the mechanism disabled to prevent further adjustment.

Figure 1:
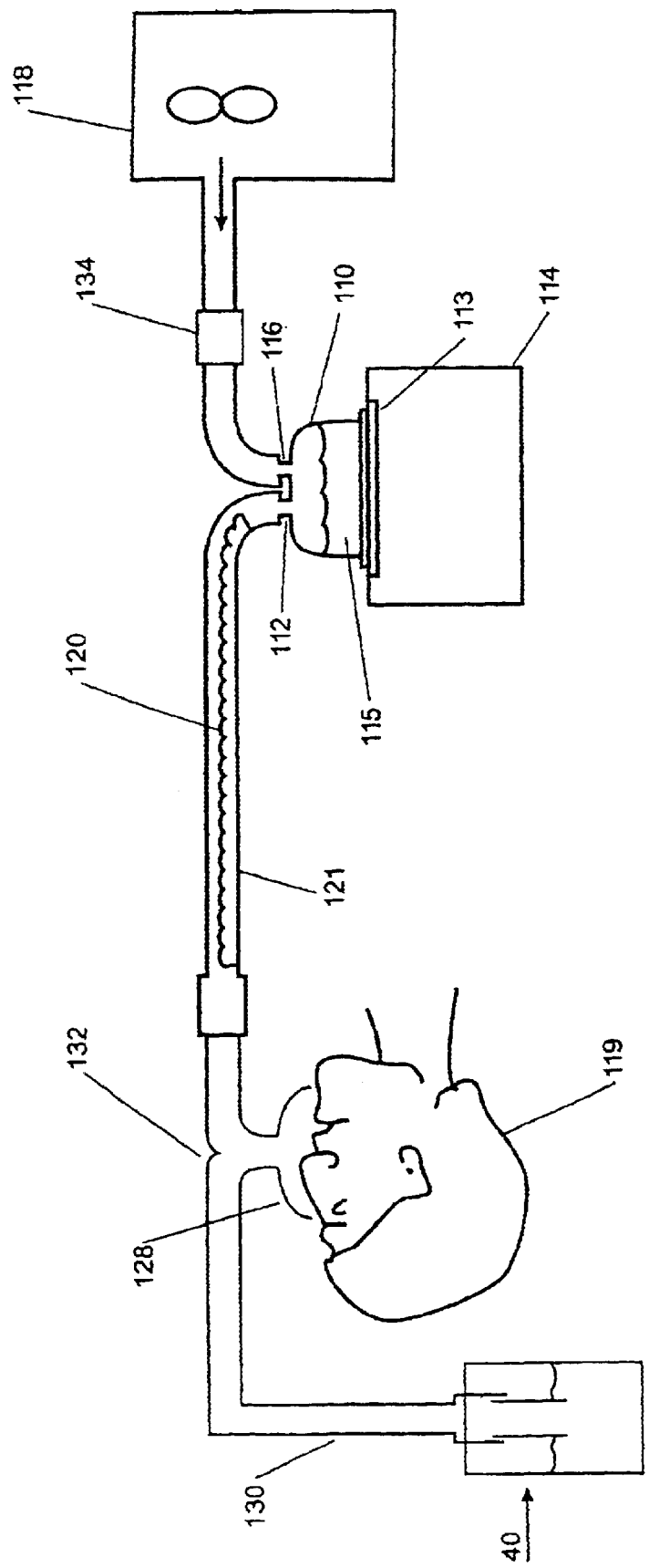
FIG. 1 is a block diagram showing a typical configuration for supplying breathing assistance to a patient.

Referring now to FIG. 1 in which a typical application is depicted. A humidified Positive End Expiratory Pressure (PEEP) system is shown in which a patient 119 is receiving humidified and pressurised gases through a nasal mask 128 (or nasal cannula) connected to a inhalatory conduit 121. It should be understood that the present invention, however, is not limited to the delivery of PEEP gases but is also applicable to other types of gases delivery systems and may not necessarily involve humidification. Inhalatory conduit 121 is connected to the outlet 112 of a humidification chamber 110 which contains a volume of water 115. Inspiratory conduit 121 may contain heating means or heater wires 120 which heat the walls of the conduit to ensure a constant humidity profile along the conduit and therefore reduce condensation of humidified gases within the conduit. As the volume of water 115 within humidification chamber 110 is heated 113, water vapour begins to fill the volume of the chamber above the water's surface and is passed out of the humidification chamber 110 outlet 112 with the flow of gases (for example air) provided from a gases supply means 118 which enters the chamber 110 through inlet 116.

The humidified gases pass through the inhalatory conduit 121 to the mask 128 (or nasal cannula) attached around the patient's 119 face. The excess gases then flow through the exhalatory conduit 130 to a column of water 40 which regulates the mean pressure level.

Pressure Regulator

Figure 2:
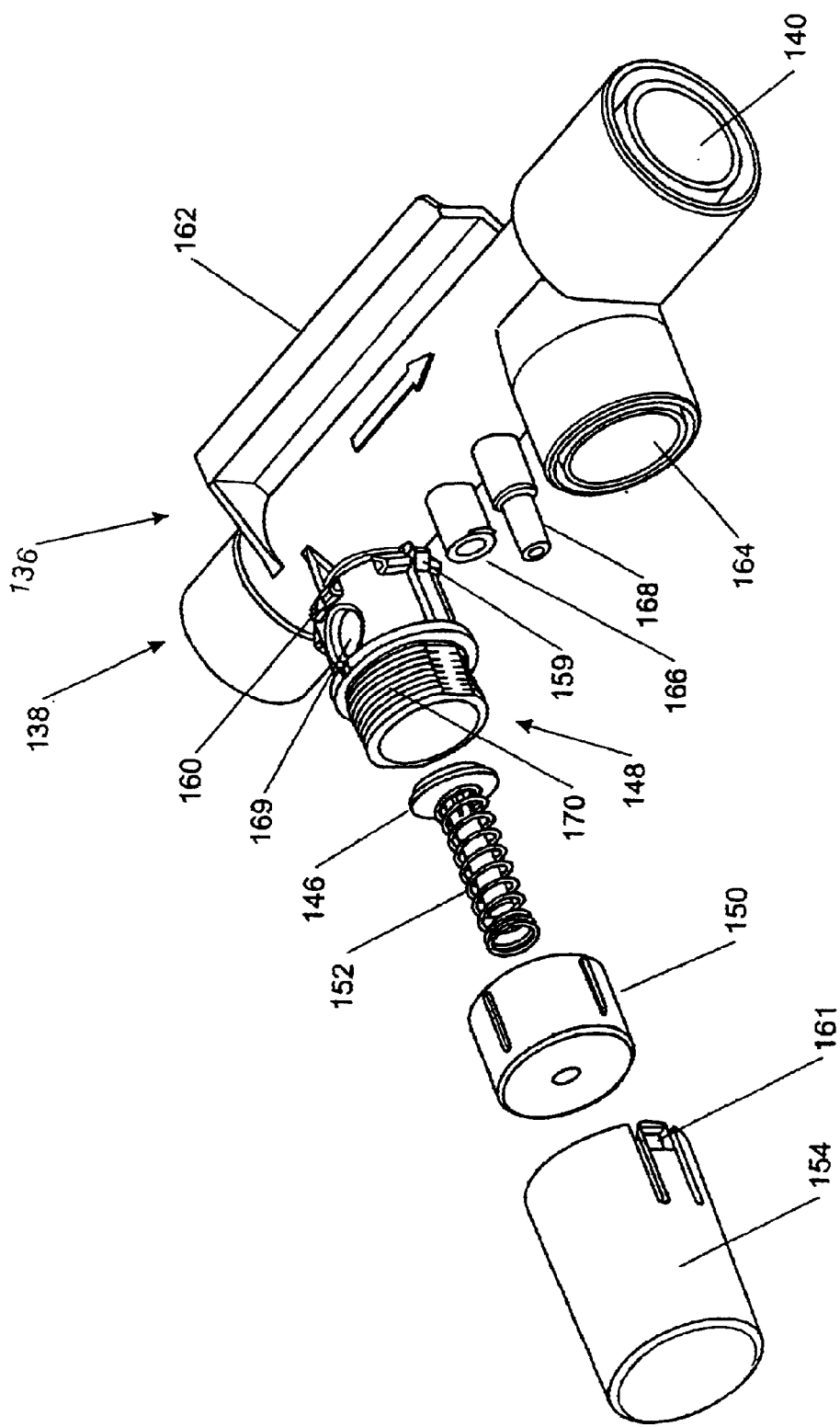
FIG. 2 is a blown out view of the pressure regulator with the lid on according to the preferred embodiment of the present invention.
Figure 3:
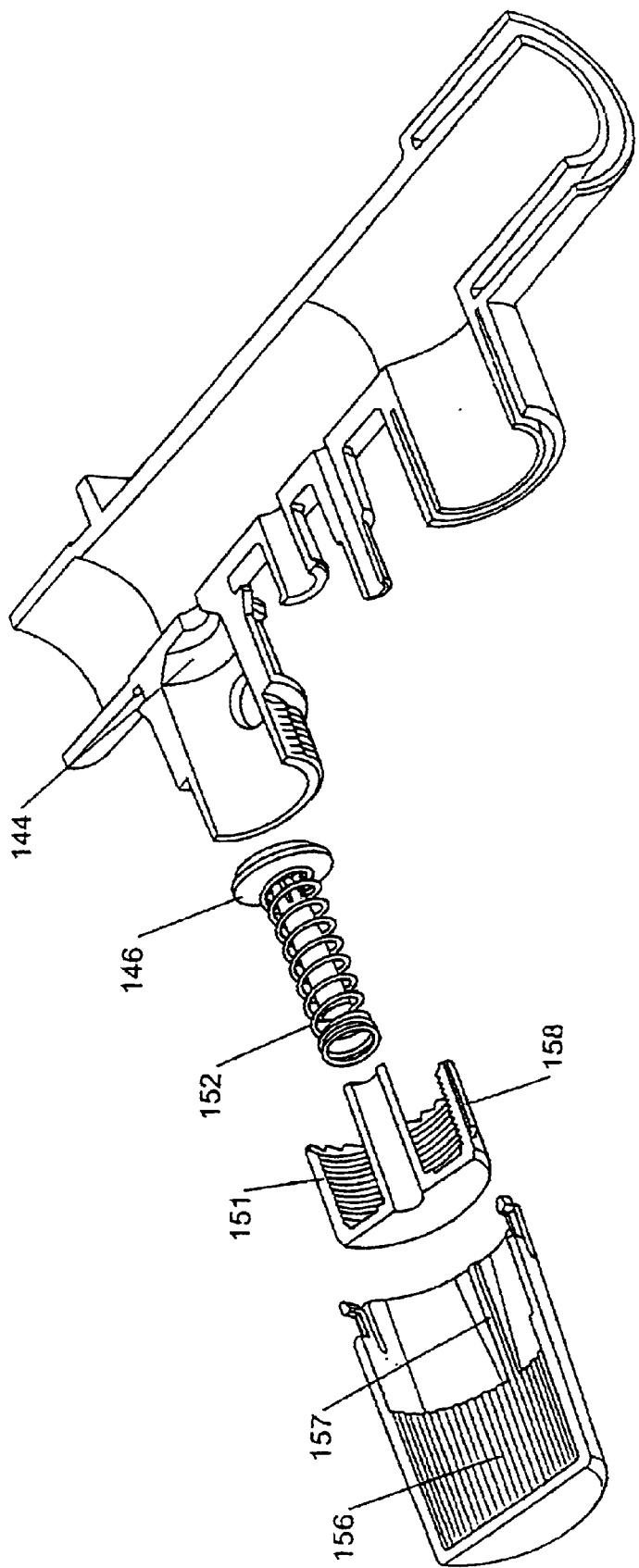
FIG. 3 is a blown out cross section of the pressure regulator according to the preferred embodiment of the present invention.

In the preferred embodiment of the present invention the pressure regulator 134, is shown in FIGS. 2 and 3 in detail. The regulator 134 includes a manifold housing 136 with an inlet 138 and an outlet 140. In the preferred embodiment the regulator 134 is disposed in the breathing circuit between the blower 118 and the humidifier 114.

The regulator 134 may either be supported by mounting bracket 162 or connected directly to humidifier inlet 116. The regulator inlet 138 is purposely a different size to outlet 140 to avoid it being connected incorrectly. Also provided are oxygen port 164, and sensor ports 166, 168 which are blocked if not in use.

The manifold housing 136 includes a hollow internal cavity running form the inlet 138 to the outlet 140. Also in fluid communication with the internal cavity 142 is a vent aperture 144 which includes a cambered surface around its periphery which acts as a valve seat for the valve plunger 146. Attached around the outside of the vent aperture 144 is the valve housing 148 which substantially in use houses the valve plunger 146. To hold the valve plunger 146 in place within the valve housing 148 the adjustment cap 150 fits over top of the valve plunger 146 and engages with the valve housing 148.

Rotation of the adjustment cap 150 about a helical thread 170 on the valve housing 148 either further compresses or expands a helical valve spring 152 which provides the restraining force on the valve plunger 146. Therefore by rotation of the adjusting cap 150 during manufacture and testing the pressure at which the valve opens can be adjusted to a desired value. The adjustment cap 150 also includes a guide channel 151 to house and guide the shaft of the plunger 146. A vent outlet 169 is provided on the housing 148 to vent the overpressure gases externally. In use it is ushered by both these caps, ensuring nothing can be introduced to obstruct the valve operation.

Once the spring has been adjusted to the desired level it may be locked in place by attaching the locking cap 154 in place over top of the adjustable cap. The locking cap 154 slides on top of the adjusting cap 150 and engages with it by virtue of a plurality of locking splines 156 disposed on its inner periphery which engage with a lesser number of locking splines 158 disposed on the outer periphery of the adjusting cap 150. Further the locking cap snaps into place and is permanently held over the valve housing 148 by virtue of the locking lip 159 which engages with the lowermost portion and locking clips 161 for the locking cap 154. Certain of the locking splines 157 on the inner periphery of the locking cap 154 extend the full length of its inner periphery to engage both the adjusting cap splines 158 as well as splines 160 on the outer periphery of the valve housing 148 to prevent any rotation.

In this fashion the adjusting cap 150 is prevented from further rotation as well as prevented from any external access. Once adjusted to the desired pressure during manufacture and testing the valve is permanently set at that pressure and may not be adjusted once locked in place. The cap 150 might be marked "Do not remove" for example, and the locking clips 161 could be purposely weakened such that removal will destroy the valve. This avoids the need to have a high tolerance spring as a spring within a relatively wider range may be adjusted to give the desired pressure.

What is claimed is:

1. A pressure regulating device for use with a breathing assistance apparatus which conveys gases to a patient requiring breathing assistance, comprising or including:

a housing including an inlet and an outlet and a venting aperture, in use said inlet and outlet being in fluid communication or integrated with a breathing apparatus, a valve member disposed within said housing, in the flow path between said inlet and said outlet, wherein the pressure of gases flowing from said inlet to said outlet being below a predetermined level said valve member blocking said vent aperture and said gases thereby flowing from said inlet to said outlet, and wherein said gases being above said predetermined level said valve member allowing at least a portion of said gases to flow through said vent aperture, an adjustment engaged with said valve member and adapted to adjust said predetermined level, and an adjustment lock adapted to engage with or about said adjustment, and adapted, such that with said adjustment lock engaged said predetermined level is permanently prevented from adjustment, is tamper evident and covers said adjustment from external observation.

2. A pressure regulating device as claimed in claim 1 wherein said valve member means comprises a valve housing, a valve member and a restraining means, wherein said pressure of gases flowing from said inlet to said outlet being below said predetermined level said restraining means biasing said valve member against said vent aperture thereby blocking said vent aperture, and wherein the pressure of said gases being above said predetermined level said restraining means biasing said valve member to a position to allow at least a portion of said gases through said vent aperture.

3. A pressure regulating device as claimed in claim 2 wherein said restraining means comprises a helical spring.

4. A pressure regulating device as claimed in claim 3 wherein said adjustment comprises a rotatable cap engaged with at least said helical spring and adapted such that in use the rotation of said rotatable cap varies the compression of said restraining means thereby changing said predetermined level.

5. A pressure regulating device as claimed in claim 4 wherein said adjustment lock comprises a locking cap adapted to prevent external access to and prevent further rotation of, said rotatable cap.

6. A breathing assistance apparatus for supplying gases to a patient to assist said patient's breathing including: a gases supply adapted to supply gases to said patient, an interface including a plurality of ports adapted to deliver said flow of gases to said patient, a conduit adapted for convey said gases from said gases supply to said interface, and a pressure regulating device disposed within or in fluid communication with said conduit, said pressure regulating device comprising or including:
a housing including an inlet and an outlet and a venting aperture, in use said inlet and outlet being in fluid communication or integrated with said conduit,
a valve member disposed within said housing, in the flow path between said inlet and said outlet, wherein the pressure of gases flowing from said inlet to said outlet being below a predetermined level said valve member blocking said vent aperture and said gases thereby flowing from said inlet to said outlet, and wherein said gases being above said predetermined level said valve member allowing at least a portion of said gases to flow through said vent aperture,
an adjustment engaged with said valve member and adapted to adjust said predetermined level, and
an adjustment lock adapted to engage with or about said adjustment, and adapted, such that with said adjustment lock engaged said predetermined level is prevented from adjustment, is tamper evident and covers said adjustment from external observation.

7. A breathing assistance apparatus as claimed in claim 6 wherein said apparatus further comprises humidification means disposed within or in fluid communication with said gases supply, said conduit and said interface, thereby humidifying said gases.

8. A method of manufacturing a system for regulating the pressure of gases supplied to a patient to assist said patient breathing comprising the steps:

assembling a valve and configuring said valve to in use relieve the pressure of said gases substantially at a predetermined pressure, adjusting said predetermined pressure to a desired pressure, and preventing further adjustment such that said predetermined pressure is permanently set.

9. A method of manufacturing a system for regulating the pressure of gases supplied to a patient to assist said patients breathing comprising the steps as claimed in claim 8 further comprising the steps of preventing external observation of said valve.

10. A method of manufacturing a system for regulating the pressure of gases supplied to a patient to assist said patients breathing comprising the steps as claimed in claim 9 further comprising the steps of preventing tampering by said patient.

* * * * *

UNITED STATES PATENT AND TRADEMARK OFFICE
CERTIFICATE OF CORRECTION

PATENT NO. : 6,644,313 B2
DATED : November 11, 2003
INVENTOR(S) : Neil Prime and Martin Leckie It is certified that error appears in the above-identified patent and that said Letters Patent is hereby corrected as shown below:

Column 1,
Line 66, "pneumothoraaes" should read -- pneumothoraces. --

Column 2,
Line 8, "eternally" should read -- externally --
Line 43, "end" should read -- and --

Signed and Sealed this

Sixteenth Day of March, 2004

JON W. DUDAS
*Acting Director of the United States Patent and Trademark Office*